United States Patent [19]

Babler

[11] Patent Number: 5,349,071
[45] Date of Patent: Sep. 20, 1994

[54] PROCESS FOR PREPARING TERTIARY ALKYNOLS

[75] Inventor: James H. Babler, Chicago, Ill.

[73] Assignee: Loyola University of Chicago, Chicago, Ill.

[21] Appl. No.: 976,219

[22] Filed: Nov. 25, 1992

[51] Int. Cl.$^5$ .................. C07C 41/26; C07C 41/30; C07C 43/30; C07D 315/00
[52] U.S. Cl. .................. 549/423; 549/416; 549/427; 568/855; 568/675; 568/662; 568/654; 568/828; 568/597; 568/592; 568/874; 556/449
[58] Field of Search ............... 568/874, 828, 855, 654, 568/662, 675, 597, 592, 828; 549/416, 427, 423; 556/449

[56] References Cited

U.S. PATENT DOCUMENTS

| | | | |
|---|---|---|---|
| 2,824,041 | 2/1958 | Bavley et al. | 568/874 |
| 3,082,260 | 3/1963 | Tedeschi et al. | 568/874 |
| 3,709,946 | 1/1973 | Tedeschi et al. | 568/874 |
| 3,755,469 | 8/1973 | Pasedach | 568/874 |

OTHER PUBLICATIONS

Trofimov, B. A., et al, *Production of Allenyl Ethers*, Chem. Abstracts 1989, vol. 111, 25313c.
Weiberth, F. J., et al, *Tandem Alkylation–Reduction, Highly Stereoselective Synthesis of (E)-1-Hydroxymethyl Methyl Propenyl Ethers from Aldehydes Using 1-Lithio-1-Methoxyallene*, J. Org. Chem. 1985, 50, pp. 5308–5314.
Isler, et al., *Vitamins and Hormones–Chemistry of Vitamin E*, vol. 20, 1962, pp. 389–405.
Burrell, et al., *Carotenoids and Related Compounds. Part XIV. Stereochemistry and Synthesis of Geraniol, Nerol, Farnesol and Phytol*, J. Chem. Soc. C, 1966, pp. 2144–2154, 1966.
Sato, et al., *A Total Synthesis of Phytol*, vol. 32, Jan., 1967, pp. 177–180.
Fujisawa, et al., *A Stereocontrolled Total Synthesis of Optically Active R,R-Phytol*, Tetrahedron Letters, vol. 22, No. 48, 1981, pp. 4823–4826.
Cohen, et al., *A Novel Total Synthesis of 2R,4'R,8'R-α-Tocopherol Vitamin E. Construction of Chiral Chromans from an Optically Active, Nonaromatic Precursor*, Journal of the American Chemical Society, 1979, pp. 6710–6716.
Chan, et al., *Synthesis of 2R,4'R,8'R-α-Tocopheryl Acetate Vitamin E Acetate Using [3,3] Sigmatropic Rearrangement*, The Journal of Organic Chemistry, vol. 43, No. 18, 1978, pp. 3435–3440.
Russell, A. and Kenyon, R. L. *Pseudoionone*, Organic Synthesis Collective vol. 3, pp. 747–750.
Haynes, L. J. and Jones, E. R. H., *Unsaturated Lactones, Part I*, J. Chem. Soc., 1946, pp. 954–957.
Sato, K., et al., Japanese Patent Application 26,656 ('63) 6,10,14–Trimethylpentadeca-6-en-4-yn-2-ol, Chem. Abstr., 1964, p. 6746(e).
*Acetylene–Alcohol*, Compendium of Organic Synthetic Methods, vol. 2, Section 302, pp. 218–220.
*Acetylene–Alcohol*, Compendium of Organic Synthetic Methods, vol. 3, Section 302, p. 337.

(List continued on next page.)

*Primary Examiner*—Johann Richter
*Assistant Examiner*—Margaret J. Page
*Attorney, Agent, or Firm*—Marshall, O'Toole, Gerstein, Murray & Borun

[57] ABSTRACT

Processes for synthesizing tertiary alkynols by reacting carbonyl-group-containing compounds with alkynes in the presence of a basic catalyst are disclosed. Preferred products are 6,10,14-trimethyl-4-pentadecyn-6-ol compounds having the structure:

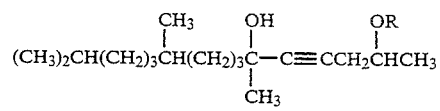

A preferred, novel compound, 6,10,14-trimethyl-4-pentadecyne-2,6-diol, can be used in the synthesis of Vitamin E or Vitamin $K_1$.

33 Claims, No Drawings

OTHER PUBLICATIONS

Solomons, T. W., *Organic Chemistry*, 5th Ed., p. 471.

March, J., *Advanced Organic Chemistry: Reactions, Mechanisms and Structure*, 4th Ed., pp. 250–252.

Solomons, T. W., *Organic Chemistry*, 5th Ed., p. 94.

Tedeschi, R. J., et al., *Base–Catalyzed Reaction of Acetylene and Vinyl–acetylenes with Carbonyl Compounds in Liquid Ammonia under Pressure*, J. Org. Chem., vol. 28, 1963, pp. 1740–1743.

Tedeschi, R. J., *The Mechanism of Base–Catalyzed Ethynylation in Donor Solvents*, J. Org. Chem., vol. 30, 1965, pp. 3045–3049.

Papa, et al., *A New Class of Hypnotics: Unsaturated Carbinols. Part I*, J. Am. Chem. Soc., vol. 76, 1954, pp. 4446–4450.

Saimoto, et al., *Regiocontrolled Formation of 4,5–Dihydro–3(2H)–furanones from 2–Butyne–1,4–diol Derivatives*, Bull. Chem. Soc. Jpn., vol. 56, 1983, pp. 3078–3087.

Miyashita, N., et al., *Pyridinium p–Toluenesulfonate, A Mild and Efficient Catalyst for the Tetrahydropyranylation of Alcohols*, J. Org. Chem., vol. 42, No. 23, 1977, pp. 3772–3774.

Claesson, A. and Bogentoft, C., *Formation of Conjugated Dienes on Lithium Aluminium Hydride Reduction of Allenic tert.–Alcohols*, Acta Chem. Scand. 26, No. 6, 1972, pp. 2540–2542.

Redel, J., et al., Fr. 1,460,512 (Dec. 2, 1966), Chem. Abstr., 67, 1964, pp. 100, 279z.

PROCESS FOR PREPARING TERTIARY ALKYNOLS

BACKGROUND OF THE INVENTION

A. Technical Field

The present invention relates generally to processes for synthesizing tertiary alkynols, in particular, 6,10,14-trimethyl-4-pentadecyn-6-ol compounds having the formula:

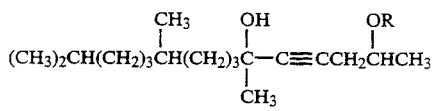

wherein "R" represents H, or an alkyl group which can be aliphatic (e.g. tert-butyl), arylalkyl (e.g. benzyl) or part of a mixed acetal derivative

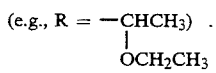

These 6,10,14-trimethyl-4-pentadecyn-6-ol compounds can be readily converted to 3,7,11,15-tetramethyl-1-hexadecen-3-ol (isophytol), an intermediate used in both the manufacture of alpha-tocopherol (the most active Vitamin E factor known to occur in nature) as well as in the synthesis of Vitamin $K_1$.

The 6,10,14-trimethyl-4-pentadecyn-6-ol compounds of the present invention can be prepared using the following novel alkylation reaction:

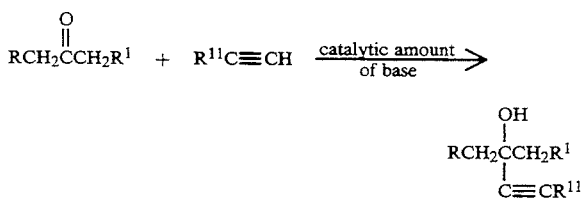

R, $R^1$ = alkyl and/or H and/or form part of an alicyclic ring (e.g., cyclohexanone).

$R^{11}$ = an alkyl, alkenyl, aryl or arylalkyl group.

The process can also be used to synthesize tertiary alkynols in addition to 6,10,14-trimethyl-4-pentadecyn-6-ol derivatives.

B. Technical Background

The addition of an acetylide anion to a ketone to yield a 3° alkynol is not a novel process per se; however, the conditions (i.e., catalytic amount of a relatively weak base) used in the present invention differ from those shown in the literature.

Numerous examples have been reported in the literature of transformations of the following type:

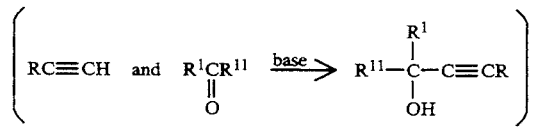

However, all such examples (except for certain reactions involving acetylene, discussed below) teach that the use of one equivalent of strong base is required for a successful reaction. Specific examples can be found in the following references:

(a) Section 302 (pages 218–220) in COMPENDIUM OF ORGANIC SYNTHETIC METHODS, VOLUME 2, edited by I. T. Harrison, et al. (John Wiley & Sons, Inc., 1974).

(b) Section 302 (page 337) in COMPENDIUM OF ORGANIC SYNTHETIC METHODS, VOLUME 3, edited by L. S. Hegedus, et al. (John Wiley & Sons, Inc., 1977).

(c) T. W. G. Solomons, ORGANIC CHEMISTRY, Fifth Edition, page 471 (John Wiley & Sons, Inc., 1992).

The commonly-held notion that one equivalent of a strong base is required for alkylation is not surprising in view of the known acidities of a terminal alkyne and representative alcohols. For example, Table 8.1 on pages 250–252 in ADVANCED ORGANIC CHEMISTRY: REACTIONS, MECHANISMS AND STRUCTURE, Fourth Edition, by J. March (John Wiley & Sons, Inc., 1992) lists the following $pK_a$ values:

| | |
|---|---|
| $R_2CHOH$ (a 2° alcohol, as found in 4-pentyn-2-ol) | 16.5 |
| $R_3COH$ (a 3° alcohol) | 17 |
| $RCOCH_2R$ (an enolizable ketone) | 19–20 |
| $HC\equiv C-H$ | 25 |
| $NH_3$ | 38 |
| $CH_3CH_2-H$ | 50 |

Similar $pK_a$ values are listed in a widely-used organic chemistry textbook: T. W. G. Solomons, ORGANIC CHEMISTRY, FIFTH EDITION, Table 3.1 on page 94 (John Wiley & Sons, Inc., 1992). Such data indicate that strong bases such as $NaNH_2$ or ethylmagnesium bromide can convert a terminal alkyne to an acetylide salt, which can subsequently be treated with a ketone to give a 3° alkynol. On the other hand, alkoxides derived from 2° and 3° alcohols are expected to be too weakly basic to convert (appreciably) a terminal alkyne to an acetylide anion. Indeed, under the reaction conditions utilized in the present invention, one would instead predict conversion of an enolizable ketone to its enolate anion.

There are a number of patents, cited in R. J. Tedeschi, et al., J. Org. Chem., 28, 1740 (1963), that at first glance seem to suggest the alkynylation step of the present invention. These patents relate to the use of potassium hydroxide (comparable in basicity to an alkoxide) as a catalyst in the reaction of gaseous acetylene or vinylacetylene with aldehydes and ketones in liquid ammonia—a process referred to as the Favorskii reaction. However, a subsequent article by R. J. Tedeschi, J. Org. Chem., 30, 3045 (1965), confirmed that the Favorskii conditions do not involve an acid-base reaction. Rather than involving the formation of an alkali metal acetylide, Tedeschi verifies the existence of an acetylene-alkali hydroxide complex in the Favorskii reaction.

In contrast, the alkynylation step of the present invention proceeds more rapidly with the strongest alkoxide bases: i.e., rates are greater when $KOC(CH_3)_3$ is used rather than $KOCH_3$; and reaction is even slower when powdered KOH is used as the basic catalyst. Moreover, unlike the Favorskii reaction, the process of the present invention proceeds poorly for several representative aldehydes, including isobutyraldehyde and benzaldehyde. Indeed, attempted use of the alkynylation process of the instant invention with benzaldehyde resulted in a significant amount of reduction of the latter compound to yield benzyl alcohol.

Attempts to alkylate 6,10-dimethyl-3,5,9-undecatrien-2-one (pseudoionone) using

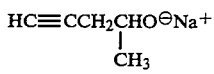

produced none of the expected 3° alkynol, nor was any unreacted pseudoionone recovered. Since alpha, be-taunsaturated ketones such as pseudoionone are known to react with alkali-metal acetylides (generated by use of strong bases) to yield 3° alkynols, the failure of the reaction when applied to pseudoionone was surprising. In contrast, the same alkylation using the related ketone, 6,10-dimethyl-2-undecanone, proceeded easily.

C. Utility of Products and Processes

F. G. Fischer and K. Löwenberg, Ann, 475, 183–204 (1929), have reported a synthesis of both isophytol and phytol utilizing the C-18 ketone (1) shown below as the key intermediate:

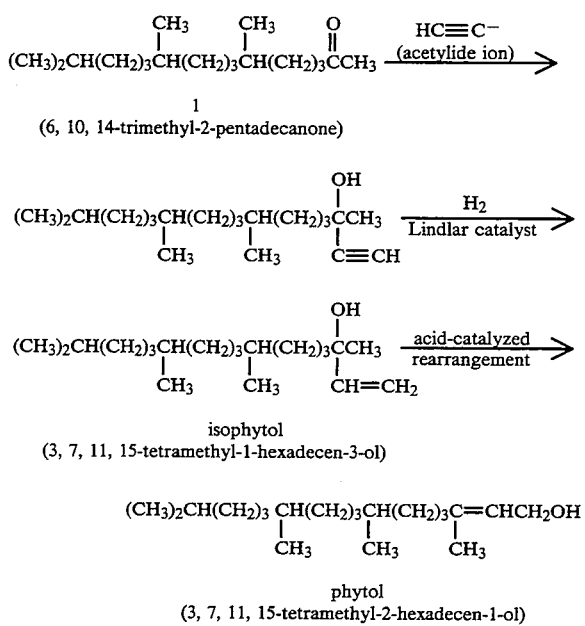

Other syntheses of phytol have been reported in the literature, but they generally require lengthy sequences of reactions.

Treatment of either phytol or isophytol with the commercially available compound, trimethylhydroquinone, and an acid catalyst affords alpha-tocopherol, as outlined below:

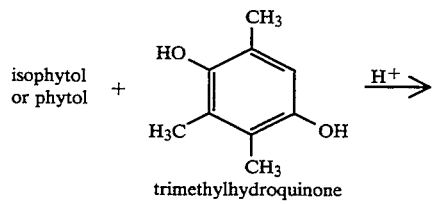

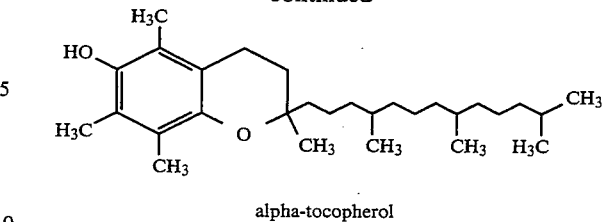

alpha-tocopherol

This synthesis is shown at pages 392-3 in *Chemistry of Vitamin E*, by O. Isler, et al., a chapter in VITAMINS AND HORMONES; ADVANCES IN RESEARCH AND APPLICATIONS, VOLUME 20, edited by R. S. Harris, et al. (Academic Press, 1962).

Other processes for synthesizing vitamins E and $K_1$ are illustrated in *Chem. Abstracts*, 67, 100,279z (1967); at pages 389–405 of VITAMINS AND HORMONES: ADVANCES IN RESEARCH AND APPLICATIONS, VOLUME 20, edited by R. S. Harris, et al. (Academic Press, 1962); in N. Cohen, et al., *J. Am. Chem. Soc.*, 101, 6710 (1979); and in K. Chan, et al., *J. Org. Chem.*, 43, 3435 (1978).

BRIEF DESCRIPTION OF THE INVENTION

1) Description of General Process

The 6,10,14-trimethyl-4-pentadecyn-6-ol compounds of the present invention can be prepared using the following novel alkylation reaction:

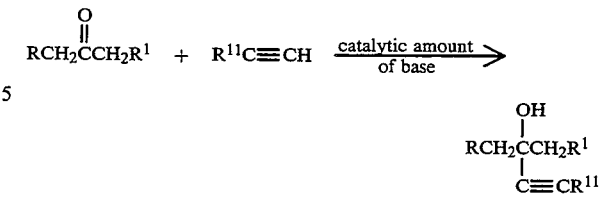

$R,R^1$ = alkyl and/or H and/or form part of an alicyclic ring (e.g., cyclohexanone).

$R^{11}$ = an alkyl, alkenyl, aryl or arylalkyl group.

Furthermore, R,R' can be functionalized with a carbon-carbon double bond (e.g., 6-methyl-5-hepten-2-one), provided that the double bond is not conjugated with the carbonyl group. Groups containing ether and acetal functionalities can also be employed. The alkyl group can contain an unblocked 3° alcohol group (e.g., 2-methyl-3-butyn-2-ol), alkoxide functionality, e.g.,

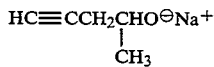

or ether (or mixed acetal) functionality, e.g.,

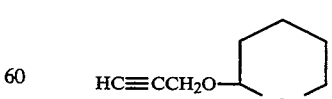

A. Suitable bases include those stronger than alkali-metal carbonates (i.e., the reaction was unsuccessful in the presence of $K_2CO_3$ as the only basic catalyst). Preferred bases are alkali-metal alkoxides, including potassium and sodium tert-butoxide. Since $KOC(CH_3)_3$ is less associated than $NaOC(CH_3)_3$, it is a more effective catalyst and is thus especially preferred. However, sodium tert-butoxide, when used in tandem with a soluble potassium salt (e.g., potassium acetate or potassium chloride), enables the reaction to proceed at a rate similar to one catalyzed by KOC(CH$_3$)$_3$ alone. Weaker basic alkoxides such as potassium methoxide also catalyze the reaction—but at a much slower rate. Powdered KOH can be used to catalyze the alkynylation reaction, but the reaction also proceeds at a slower rate. Obviously, a catalytic amount of a base that is stronger than an alkoxide (e.g., NaNH$_2$) can be employed. Finally, use of an additional basic catalyst is unnecessary if one of the reactants contains alkoxide functionality, e.g.,

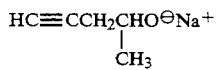

which itself can serve as a catalyst for the reaction.

B. Suitable solvents comprise non-hydroxylic organic liquids such as dimethyl sulfoxide, 1-methyl-2-pyrrolidinone and acetonitrile-i.e., polar, aprotic solvents which accelerate the reaction significantly. However, the reaction proceeds in less polar solvents such as tetrahydrofuran or even benzene—although heating the mixture to a moderate temperature (approximately 60° C.) may be necessary when using such solvents to complete the reaction. Water and alcohols (i.e., hydroxylic solvents) are not suitable for this alkynylation process. The presence of water (5% v/v) in dimethyl sulfoxide virtually stops the reaction from proceeding.

C. Reaction temperature: The reaction is complete in several hours if it is conducted at 20° C. in a polar, aprotic solvent such as DMSO. Gentle heating (i.e., temperatures less than 100° C.) can accelerate the reaction in less polar solvents.

D. Side-reactions were minimal in virtually all systems examined. However, when a methyl ketone, i.e.,

was used as a reactant, it was necessary to add the methyl ketone slowly to the solution containing the terminal alkyne and the basic catalyst in order to avoid aldol condensations.

E. Substrates: In addition to the preferred alkynediol (6) (whose synthesis is described infra), the following alkynols were prepared by the foregoing novel alkylation process using the reagents specified below:
  (i) cyclohexanone and 1-octyne→1-(1-octynyl)cyclohexanol
  (ii) cyclohexanone and 1-hexyne→1-(1-hexynyl)cyclohexanol
  (iii) 3-pentanone and phenylacetylene →3-ethyl-1-phenyl-1-pentyn-3-ol
  (iv) cyclohexanone and 2-methyl-3-butyn-2-ol →1-(3-hydroxy-3-methyl-1-butynyl)cyclohexanol
  (v) cyclohexanone and 3-[(tetrahydropyran-2-yl)oxy]propyne→1-[3-[(tetrahydro-2H-pyran-2-yl)oxy]-1-propynyl]cyclohexanol.

2) Description of Preferred Processes

A. Preparation of 6,10,14-trimethyl-4-pentadecyne-2,6-diol from citral.

A method of preparing a preferred, novel compound, 6,10,14-trimethyl-4-pentadecyne-2,6-diol (6), using citral as a starting material, is outlined below. Compound (6), in turn, can be easily converted to isophytol.

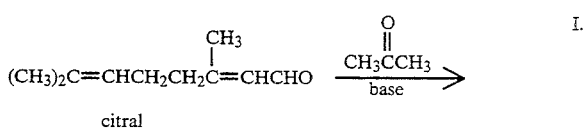

citral

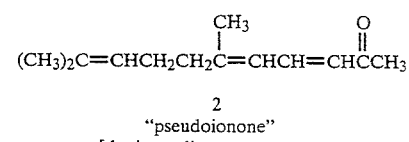

2
"pseudoionone"
[the immediate precursor to beta-ionone, for vitamin A synthesis]

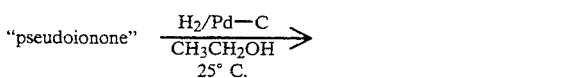

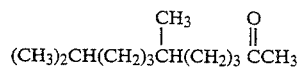

3
[94% yield from 2 on a "15-20 gram" scale]

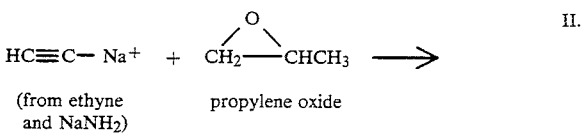

(from ethyne and NaNH$_2$)    propylene oxide

4

The yield of 4 was reported to be greater than 50% in an old literature reference: L. J. Haynes and E. R. H. Jones, *J. Chem. Soc.*, 954 (1946). Compound 4 (4-pentyn-2-ol) is commercially available form Aldrich, Fluka, Lancaster Synthesis and others as a specialty chemical.

III. Coupling the Products from I and II:

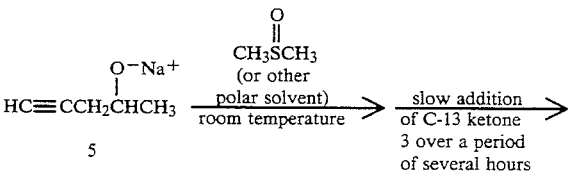

[Reaction proceeds quickly at 20° C. if 4 is converted to its sodium salt (5) by treatment with sodium hydride or metallic sodium. No other base is necessary under such conditions.]

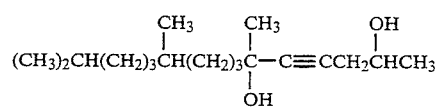

6
>95% yield

As noted above, when alkylation step III is attempted with terminal alkynes which do not posses alkoxide functionality capable of catalyzing the process (e.g., 1-octyne or phenylacetylene), the presence of a catalytic amount of an alkoxide base is required. Potassium tert-butoxide is preferred since in its presence the reaction occurs very rapidly at room temperature. However, other alkoxide bases, including sodium tert-butoxide or potassium methoxide, can be used successfully to catalyze this alkynylation. If one desires to avoid the use of potassium tert-butoxide as a catalyst, identical results (i.e., fast reaction at room temperature) can be obtained if it is replaced by catalytic amounts of sodium tert-butoxide and a soluble potassium salt such as potassium acetate (prepared from KOH and acetic acid).

Preparation of 6,10,14-trimethyl-4-pentadecyne-2,6-diol using blocking groups.

An alternate method to conduct this alkylation step involves initial blocking of the hydroxyl group in alkynol 4 by conversion, for example, to a benzyl ether derivative (using benzyl chloride) and adding a catalytic amount of an alkoxide base to promote coupling of the terminal alkyne with C-13 ketone 3:

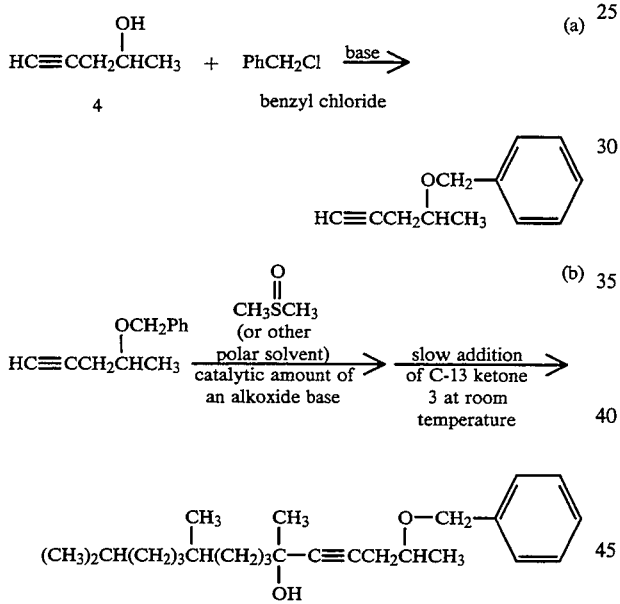

After dehydration of the 3° alcohol functionality, this product, 2-benzyloxy-6,10,14-trimethyl-4-pentadecyn-6-ol, can be converted to toluene and 6,10,14-trimethyl-2-pentadecanol by catalytic hydrogenation.

In lieu of a benzyl ether blocking group, alternative blocking groups for the hydroxyl functionality could be employed in this reaction. Examples include: tert-butyl, trialkylsilyl and mixed acetal groups. Other blocking groups will be apparent to a chemist of ordinary skill.

C. Conversion of 6,10,14-trimethyl-4-pentadecyne-2,6-diol to 6,10,14-trimethyl-2-pentadecanone Diol (6) (6,10,14-trimethyl-4-pentadecyne-2,6-diol) can be converted to a C-18 ketone, 6,10,14-trimethyl-2-pentadecanone using the following procedure:

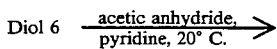

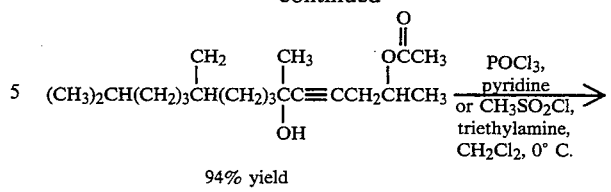

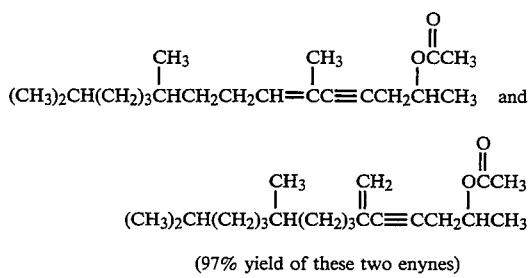

(97% yield of these two enynes)

The acetate ester in these two enynes was hydrolyzed by use of potassium carbonate in aqueous methyl alcohol at room temperature to give, in 93% yield, a 2:1 mixture of enynols 7:8 respectively:

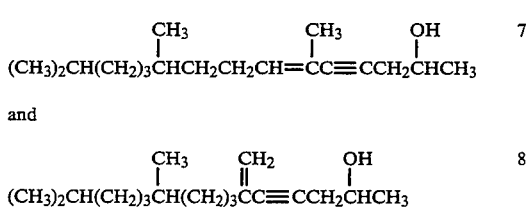

There is no need to separate 7 and 8 since subsequent hydrogenation (H₂/Pd-C) yields the same saturated C-18 alcohol:

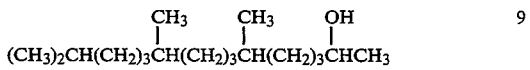

(easily oxidized to the C-18 ketone, 6,10,14-trimethyl-2-pentadecanone, by various known methods, cited below).

Enynol Z has previously been prepared as part of an alternate route to isophytol: S. Abe, Japanese Patent No. 26,656 (Dec. 23, 1963). See: *Chem. Abstracts*, 60, 6746e (1964). This Japanese patent reference reported the preparation of 3,7,11-trimethyl-3-dodecen-1-yne in several steps from citral and its subsequent coupling (using one equivalent of a very strong base) to propylene oxide. The latter step proceeded in 50% yield.

3) Large-scale Process

On an industrial scale, the following sequence of reactions can be employed to convert 6,10,14-trimethyl-4-pentadecyne-2,6-diol (6) to 6,10,14-trimethyl-2-pentadecanol which, in turn, can be easily oxidized to 6,10,14-trimethyl-2-pentadecanone:

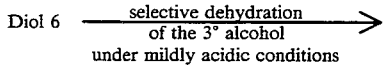

. If this occurs, the following sequence of steps should produce the desired intermediate:

1) 6 $\xrightarrow{H_2/Pd-C}$ (to saturate triple bond)

2) $\xrightarrow[\text{as CuSO}_4\text{), heat}]{\text{KHSO}_4 \text{ or other mild acid catalyst (such}}$

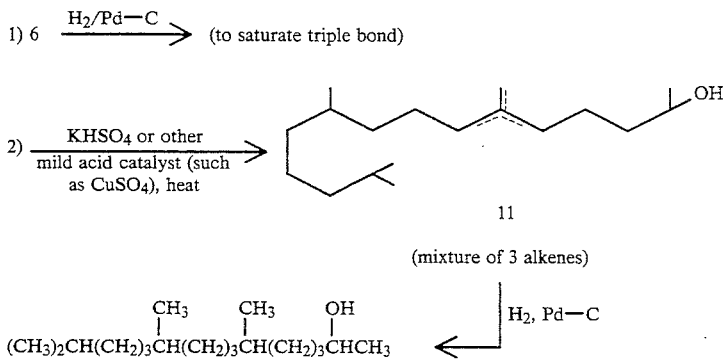

11

(mixture of 3 alkenes)

$$\xleftarrow{H_2, Pd-C} \underset{9}{(CH_3)_2CH(CH_2)_3\overset{\overset{CH_3}{|}}{C}H(CH_2)_3\overset{\overset{CH_3}{|}}{C}H(CH_2)_3\overset{\overset{OH}{|}}{C}HCH_3}$$

and $$\underset{8}{(CH_3)_2CH(CH_2)_3\overset{\overset{CH_2}{\|}}{\underset{\underset{CH_3}{|}}{C}}(CH_2)_3C\equiv CCH_2\overset{\overset{OH}{|}}{C}HCH_3}$$

The literature discloses conditions used to dehydrate similar 3° alcohols:

$$HC\equiv C\overset{\overset{OH}{|}}{C}(CH_3)_2 \text{ and } (CH_3)_2C=CHCH_2CH_2\overset{\overset{OH}{|}}{\underset{\underset{CH_3}{|}}{C}}-C\equiv CH$$

Subsequent hydrogenation (H$_2$/Pd-C) yields the same saturated C-18 alcohol:

7 and 8 $\xrightarrow[CH_3CH_2OH]{H_2/Pd-C}$ $$\underset{9}{(CH_3)_2CH(CH_2)_3\overset{\overset{CH_3}{|}}{C}H(CH_2)_3\overset{\overset{CH_3}{|}}{C}H(CH_2)_3\overset{\overset{OH}{|}}{C}HCH_3}$$

[easily oxidized to "phytone", the
C-18 immediate precursor to isophytol;
for one such method, see S. Abe,
Japanese Patent No. 26,656 (12/23/63)].

Other methods used to oxidize 2° alcohol 9 "phytone" include:
(a) aqueous NaOCl (bleach) in acetic acid; such conditions give >95% yield of 2-octanone from 2-octanol. See: *J. Org. Chem.*, 45, 2030 (1980).
(b) excess acetone with a catalytic amount of aluminum isopropoxide; such conditions are used on an industrial scale in the manufacture of carotenoids. For some examples, see:
  (i) *J. Org. Chem.*, 47, 2133 (1982);
  (ii) *Pure & Applied Chem.*, 51, 871 (1979);
  (iii) *Helv. Chim. Acta*, 63, 10 (1980) .
(c) air, with a transition—metal catalyst. See: *J. Chem. Soc. Chem. Commun.*, 157 (1977).
(d) aqueous H$_2$O$_2$ with a catalytic amount of WO$_4^{-2}$. See: *J. Org. Chem.*, 51, 2661 (1986).

Dehydration of 3° acetylenic alcohol 6 might be complicated by a possible "Meyer-Schuster Rearrangement". See: *Chem. Rev.*, 71, 429 (1971); *Ann. Chim.* (Paris) , 8, 178 (1963); *Russ. Chem. Rev.*, 36, 670 (1967)

DETAILED DESCRIPTION OF THE INVENTION

The following examples are presented for purposes of illustration and should not be construed as limiting the invention which is delineated in the claims.

EXAMPLE I

Preparation of 1-(1-Octynyl)cyclohexanol Using a Catalytic Amount of Various Bases in Dimethyl Sulfoxide To a solution of 546 mg (4.95 mmoles) of 1-octyne (commercially available from Aldrich Chemical Co., Milwaukee, Wis.) and 0.50 mL (4.82 mmoles) of cyclohexanone in 3.00 mL of dimethyl sulfoxide (HPLC-grade) was added 110 mg (0.98 mmole) of potassium tert-butoxide (purchased from Lancaster Synthesis, Windham, N.H.). This mixture was subsequently stirred, while being maintained under a nitrogen atmosphere, at room temperature for 5 hours. The mixture was then diluted with 25 mL of 10% aqueous sodium chloride and the product was isolated by extraction with 25 mL of 4:1 (v/v) hexane: ether. After subsequent washing of the organic layer with 10% aqueous sodium chloride (3×25 mL), it was dried over anhydrous magnesium sulfate and filtered. Removal of the volatile organic solvents by evaporation at reduced pressure, followed by removal of unreacted 1-octyne and cyclohexanone at a more significantly reduced pressure (0.25 mm), afforded 508 mg (50% yield) of the named 3° alcohol, shown by IR and proton NMR analysis to be contaminated by trace amounts of unreacted cyclohexanone. An identical experiment conducted for 19 hours at room temperature afforded 839 mg (84% yield) of the named alcohol, after purification by evaporative distillation: boiling point 110°-122° C. (bath temperature, 0.25 mm). The identity and purity of this compound were ascertained by IR and proton NMR analysis. An alternate synthesis of this alcohol has been described by H. G. Viehe, et al., *Ber.*, 95, 2557-62 (1962).

To determine the effect of other bases as catalysts in this alkynylation reaction, identical experiments were conducted using 4.95 mmoles of 1-octyne, 4.82 mmoles of cyclohexanone and 1.0 mmole of the basic catalyst in 3.00 mL of dimethyl sulfoxide (HPLC-grade). Potassium methoxide (purchased from Aldrich Chemical Co., Milwaukee, Wis.) was shown to be an effective catalyst for this alkynylation process, although not as effective as potassium tert-butoxide since the product (382 mg) isolated after a reaction time of 5 hours at room temperature was shown to be a 2:1 mixture of the named alcohol: unreacted cyclohexanone (i.e., reaction was approximately 30% complete). Slightly less effective than potassium methoxide was powdered potassium hydroxide (A.C.S. reagent, 85%). After a reaction time of 6 hours at room temperature, use of the latter base afforded 386 mg of a product shown by IR and proton NMR analysis to be a 1:1 mixture of the named alcohol: unreacted cyclohexanone (i.e., reaction was approximately 25% complete). Use of potassium carbonate as a catalyst for this process proved ineffective, since even after a prolonged reaction time (45 hours at room temperature) only a minor amount (5%, at best) of the named alcohol was produced.

Sodium alkoxide bases were also tested in this alkynylation process and ascertained to be effective, although the rate of the reaction was significantly lower than that observed with the corresponding potassium alkoxide as the catalyst (i.e., the latter reaction proceeded approximately 5 times faster). For example, use of sodium methoxide (1.0 mmole) as the catalyst afforded only 15% of the desired 3° alkynol after a reaction time of 23 hours at room temperature. Likewise, sodium tert-butoxide (commercially available from Strem Chemicals, Inc., Newburyport, Mass.) proved to be less effective than potassium tert-butoxide. Nevertheless, by conducting the reaction at 55° C. (external oil bath temperature) for 5 hours, use of sodium tert-butoxide (1.0 mmole) as the catalyst afforded the named alkynol in approximately 60% yield. Since a minor amount (<10%) of aldol condensation of cyclohexanone occurred when the alkynylation was conducted at higher temperature, it would be desirable to add the ketone slowly to the reaction mixture whenever the experiment is conducted at a temperature exceeding 25° C.

EXAMPLE II

Preparation of 1-(1-Octynyl)cyclohexanol Using a Catalytic Amount of Potassium tert-Butoxide in Various Solvents To a solution of 576 mg (5.23 mmoles) of 1-octyne and 0.50 mL (4.82 mmoles) of cyclohexanone in 3.00 mL of tetrahydrofuran (HPLC-grade, purchased from Aldrich Chemical Co., Milwaukee, Wis.) was added 118 mg (1.05 mmoles) of potassium tert-butoxide. This mixture was subsequently stirred, while being maintained under a nitrogen atmosphere, at room temperature for 21 hours. Isolation of the product as described in the procedure of Example I afforded, after removal of unreacted 1-octyne and cyclohexanone at greatly reduced pressure, 464 mg (46% yield) of the named alkynol, shown by IR and proton NMR analysis to be contaminated by trace amounts of unreacted cyclohexanone. Since an identical experiment conducted in the more polar solvent, dimethyl sulfoxide, had proceeded to completion, use of tetrahydrofuran as a solvent for this alkynylation process will require a longer reaction time and/or a higher reaction temperature. The effectiveness of the latter in accelerating the reaction was demonstrated by the use of benzene (3.0 mL) as the reaction solvent. Using the standard conditions [5.1 mmoles of 1-octyne, 4.82 mmoles of cyclohexanone and 1.0 mmole of potassium tert-butoxide in 3.00 mL of benzene (spectrophotometric-grade)], the reaction was approximately 35% complete after 20 hours at room temperature. However, when an identical experiment was conducted at 55° C. (external oil bath temperature), the conversion to the named alkynol was approximately 60%.

To verify that hydroxylic solvents were not suitable for this alkynylation process, a mixture of 5.21 mmoles of 1-octyne, 4.82 mmoles of cyclohexanone and 1.0 mmole of potassium tert-butoxide in 3.00 mL of dimethyl sulfoxide containing 0.10 mL of water was stirred for 20 hours at room temperature and resulted in a conversion of only 15% to the named alkynol. Since an identical experiment conducted in the absence of water had proceeded to completion, the presence of even minor amounts [3% (v/v)] of water dramatically slows the reaction. Similar results (i.e., very slow formation of the desired alkynol) were obtained in an experiment conducted using 9:1 (v/v) dimethyl sulfoxide: 2-butanol as the solvent, confirming the fact that only non-hydroxylic solvents are suitable for the alkynylation process.

EXAMPLE III

Preparation of 1-(1-Hexynyl)cyclohexanol Using a Catalytic Amount of Potassium tert-Butoxide in Dimethyl Sulfoxide To a solution of 420 mg (5.11 mmoles) of 1-hexyne (commercially available from Aldrich Chemical Co., Milwaukee, Wis.) and 0.50 mL (4.82 mmoles) of cyclohexanone in 3.00 mL of dimethyl sulfoxide (HPLC-grade) was added 134 mg (1.19 mmoles) of potassium tert-butoxide. This mixture was subsequently stirred, while being maintained under a nitrogen atmosphere, at room temperature for 3 hours. Isolation of the product as described in the procedure of Example I afforded, after removal of all unreacted 1-hexyne at reduced pressure, 473 mg of an approximately 2:1 mixture of the named alkynol: unreacted cyclohexanone (i.e., the conversion to the desired product was approximately 40%). An identical experiment conducted for 21 hours at room temperature afforded 603 mg (69% yield) of the named alkynol, the identity and purity of which were ascertained by IR and proton NMR analysis. An alternate synthesis of this alcohol has been reported by M. Duchon D'Engenieres, et al., *Bull. Soc. Chim. Fr.*, 201–204 (1968).

EXAMPLE IV

Preparation of 1-(1-Hexynyl)cyclohexanol Using a Catalytic Amount of Potassium tert-Butoxide in Hydroxylic Solvents To a solution of 424 mg (5.16 mmoles) of 1-hexyne and 0.50 mL (4.82 mmoles) of cyclohexanone in 3.00 mL of tert-butyl alcohol (99.5%, purchased from Aldrich Chemical Co., Milwaukee, Wis.) was added 127 mg (1.13 mmoles) of potassium tert-butoxide. This mixture was subsequently stirred, while being maintained under a nitrogen atmosphere, at room temperature for 3 hours. Isolation of the product as described in the procedure of Example I afforded little, if any, of the named alkynol. An identical experiment was conducted using 3.00 mL of 11:1 (v/v) dimethyl sulfoxide: water as the solvent in lieu of tert-butyl alcohol and afforded only a small amount (5% or less) of the named alkynol.

EXAMPLE V

Preparation of 3-Ethyl-1-phenyl-1-pentyn-3-ol

To a solution of 521 mg (5.10 mmoles) of phenylacetylene (purchased from Aldrich Chemical Co., Milwaukee, Wis.) and 0.50 mL (4.72 mmoles) of 3-pentanone in 3.00 mL of dimethyl sulfoxide (HPLC-grade) was added 113 mg (1.01 mmoles) of potassium tert-butoxide. This mixture was subsequently stirred, while being maintained under a nitrogen atmosphere, at room temperature for 21 hours. Isolation of the product as described in the procedure of Example I afforded, after evaporative distillation, 552 mg (62% yield) of the named alkynol: boiling point 97°–112° C. (bath temperature, 0.25 mm). The identity and purity of this compound were ascertained by IR and proton NMR analysis. An alternate synthesis of this alkynol has been described by D. Papa, et al., *J. Am. Chem. Soc.* 76, 4446–50 (1954).

EXAMPLE VI

Preparation of 1-(3-Hydroxy-3-methyl-1-butynyl)cyclohexanol

To a solution of 0.50 mL (5.03 mmoles) of 2-methyl-3-butyn-2-ol (purchased from Aldrich Chemical Co., Milwaukee, Wis.) and 0.50 mL (4.82 mmoles) of cyclohexanone in 3.00 mL of dimethyl sulfoxide (HPLC-grade, purchased from Aldrich Chemical Co., Milwaukee, Wis.) was added 113 mg (1.01 mmoles) of potassium tert-butoxide. This mixture was subsequently stirred, while being maintained under a nitrogen atmosphere, at room temperature for 21 hours. The mixture was then diluted with 25 mL of 10% aqueous sodium chloride and the product was isolated by extraction with 25 mL of 4:1 (v/v) ether: dichloromethane. After subsequent washing of the organic layer with 10% aqueous sodium chloride (3×25 mL), it was dried over anhydrous magnesium sulfate and filtered. Removal of the volatile organic solvents by evaporation at reduced pressure, followed by evaporative distillation, afforded 462 mg (53% yield) of the named alkynediol: boiling point 108°–120° C. (bath temperature, 0.25 mm). The identity and purity of this compound were ascertained by IR and proton NMR analysis. A previous synthesis of this diol has been reported by H. Saimoto, et al., *Bull. Chem. Soc. Jpn.*, 56, 3078–3087 (1983).

The moderate yield of alkynediol obtained in this experiment perhaps reflects the anticipated (in view of Example IV) diminished reactivity of acetylide anions in the presence of a hydroxylic functionality (i.e., the unblocked 3° alcohol moiety in 2-methyl-3-butyn-2-ol).

EXAMPLE VII

Preparation of 1-[3-(Tetrahydropyran-2-yl)oxy-1-propynyl]cyclohexanol

To a solution of 704 mg (5.02 mmoles) of 3-[(tetrahydropyran-2-yl)oxy]propyne [prepared from 2-propyn-1-ol and dihydropyran in the presence of a catalytic amount of pyridinium tosylate, using a procedure described by N. Miyashita, et al., *J. Org. Chem.*, 42, 3772 (1977)] and 0.50 mL (4.82 mmoles) of cyclohexanone in 3.00 mL of dimethyl sulfoxide (HPLC-grade) was added 114 mg (1.02 mmoles) of potassium tert-butoxide. This mixture was subsequently stirred, while being maintained under a nitrogen atmosphere, at room temperature for 21 hours. Isolation of the product as described in the procedure of Example I afforded, after evaporative distillation, 1.047 g (91% yield) of the named alkynol: boiling point 120°–138° C. (bath temperature, 0.25 mm). The identity and purity of this compound were ascertained by high-field (300 MHz) proton NMR analysis. An alternate synthesis of this alkynol has been described by A. Claesson, et al., *Acta Chem. Scand.*, 26, 2540–42 (1972).

In an identical experiment using 2-propyn-1-ol in lieu of 3-[(tetrahydropyran-2-yl)oxy]propyne (i.e., not blocking the 1° alcohol functionality in 2-propyn-1-ol by conversion to its tetrahydropyranyl ether derivative), the adduct between cyclohexanone and 2-propyn-1-ol was obtained, but the reaction rate was too slow at room temperature (less than 30% conversion after 2 days at room temperature). This result is consistent with the previous observations (Example IV) that the alkynylation process is sluggish in the presence of hydroxylic solvents.

EXAMPLE VIII

Preparation of 1-(1-Octynyl)cyclohexanol Using Catalytic Amounts of Sodium tertbutoxide and Potassium Acetate at Room Temperature Since alkynylation of cyclohexanone using 1-octyne in the presence of a catalytic amount of sodium tert-butoxide in dimethyl sulfoxide was slow at room temperature (see Example I), the following experiment was conducted to determine if the addition of a soluble potassium salt (e.g., potassium acetate or potassium bromide) would accelerate the process, thereby obviating the need to heat the reaction mixture.

To a solution of 555 mg (5.04 mmoles) of 1-octyne and 0.50 mL (4.82 mmoles) of cyclohexanone in 3.00 mL of dimethyl sulfoxide (HPLC-grade) were added, 98 mg (1.02 mmoles) of sodium tert-butoxide (purchased from Strem Chemicals, Inc., Newburyport, Mass.) and 86 mg (0.88 mmole) of potassium acetate (A.C.S. reagent-grade, purchased from Aldrich Chemical Co., Milwaukee, Wis.). This mixture was subsequently stirred, while being maintained under a nitrogen atmosphere, at room temperature for 5 hours. Isolation of the product as described in the procedure of Example I afforded 451 mg (45% yield of the named alkynol, after removal of unreacted 1-octyne and cyclohexanone at significantly reduced pressure (0.25 mm). These results, when compared to those described in Example I, indicate that sodium tert-butoxide, accompanied by a potassium salt such as potassium acetate, can be as efficient a catalyst for this alkynylation process as is potassium tert-butoxide.

EXAMPLE IX

Alkynylation of a Methyl Ketone: Preparation of 2,4-Dimethyl-5-dodecyn-4-ol

To a solution of 0.75 mL (5.08 mmoles) of 1-octyne and 112 mg (1.12 mmoles) of 4-methyl-2-pentanone (purchased from Aldrich Chemical Co., Milwaukee, Wis.) in 3.00 mL of anhydrous tetrahydrofuran was added 104 mg (0.93 mmole) of potassium tert-butoxide. This mixture was subsequently stirred, while being maintained under a nitrogen atmosphere, at room temperature for 4.5 hours. Isolation of the product as described in the procedure of Example I, followed by removal of unreacted 1-octyne and 4-methyl-2-pentanone at significantly reduced pressure (0.25 mm) afforded 80 mg (34% yield) of the named alkynol, shown by IR and proton NMR analysis to be contaminated by a minor amount of material derived from an aldol condensation of 4-methyl-2-pentanone. A similar experiment that was conducted using 0.60 mL (4.80 mmoles) of 4-methyl-2-pentanone and 557 mg (5.05 mmoles) of 1-octyne (i.e., stoichiometric amounts of ketone and terminal alkyne) afforded a product mixture containing a substantial amount of "aldol condensation material". To avoid this latter side-reaction, alkynylation of methyl ketones should be conducted at low concentration of ketone—i.e., slow addition of ketone, over a prolonged time, to the other reagents or use of a large excess of alkyne (when conducting a small-scale reaction).

EXAMPLE X

Alkynylation of Representative Aldehydes Using a Catalytic Amount of Potassium tert-Butoxide in Dimethyl Sulfoxide To a solution of 1.00 mL (8.70 mmoles) of 1-hexyne and 0.50 mL (4.92 mmoles) of benzaldehyde in 4.00 mL of dimethyl sulfoxide (HPLC-grade) was added 115 mg (1.02 mmoles) of potassium tert-butoxide. This mixture was subsequently stirred, while being maintained under a nitrogen atmosphere, at room temperature for 45 hours. Isolation of the product as described in the procedure of Example I afforded 474 mg of a mixture, shown by IR and proton NMR analysis to contain both unreacted benzaldehyde and a substantial amount of benzyl alcohol (an indication that reduction of the aldehyde functionality was occurring under the reaction conditions), along with the desired alkynol: 1-phenyl-2-heptyn-1-ol. Fractional evaporative distillation afforded 245 mg (27% yield) of the latter alkynol: boiling point 110°–123° C. (bath temperature, 0.25 mm), the identity of which was ascertained by IR and proton NMR analysis.

Attempts to alkynylate isobutyraldehyde and propionaldehyde under similar conditions also gave poor results—i.e., mixtures of products.

EXAMPLE XI

Attempted Alkynylation of Propylene Oxide

To a solution of 1.00 mL (6.78 mmoles) of 1-octyne and 0.50 mL (7.15 mmoles) of propylene oxide in 4.00 mL of dimethyl sulfoxide was added 155 mg (1.38 mmoles) of potassium tert-butoxide. This mixture was subsequently stirred, while being maintained in a pressure bottle under a nitrogen atmosphere, at room temperature for 41 hours. Isolation of the product as described in the procedure of Example I afforded, after removal of unreacted 1-octyne at reduced pressure, 153 mg of material, shown by IR and proton NMR analysis to contain little (if any) of the desired alkynol: 4-undecyn-2-ol. Instead, spectral analysis indicated that the product was derived by attack of tert-butoxide on the oxirane ring of propylene oxide.

EXAMPLE XII

Catalytic Hydrogenation of Pseudoionone

A mixture of 17.82 g (92.8 mmoles) of 6,10-dimethyl-3,5,9-undecatrien-2-one ("pseudoionone", prepared from citral and acetone as described by A. Russell, et al., *Organic Syntheses, Collective Volume 3*, pages 747–750) and 1.0 g of 5% palladium on activated carbon in 50 mL of absolute ethyl alcohol was shaken vigorously under a hydrogen atmosphere (approximately 2–3 atm. pressure) for 30 minutes. After removal of the catalyst by filtration through a small pad of Hyflo Super-Cel ® filtering aid, the filtrate was diluted with 150 mL of hexane. The organic layer was subsequently washed with water (2×400 mL), then dried over anhydrous magnesium sulfate, and re-filtered. Removal of the hexane by evaporation at reduced pressure, followed by distillation, afforded 15.95 g (87% yield) of 6,10-dimethyl-2-undecanone: boiling point 68°–72° C. at 0.15 mm. A previous synthesis of the latter ketone has been reported by F. G. Fischer, et al., *Ann.*, 475, 183 (1929).

EXAMPLE XIII

Preparation of 4-Benzyloxy-1-pentyne

A solution of 1.00 mL (10.6 mmoles) of 4-pentyn-2-ol (purchased from Aldrich Chemical Co., Milwaukee, Wis.) in 4.0 mL of anhydrous tetrahydrofuran was added dropwise slowly over 10 minutes to a stirred mixture of 522 mg (13.05 mmoles) of sodium hydride (60% dispersion is mineral oil, which was removed prior to the reaction by washing with hexane), 56 mg (0.15 mmole) of tetrabutylammonium iodide, and 2.0 mL of anhydrous tetrahydrofuran, protected from atmospheric moisture and maintained at a temperature of 10°–15° C. by use of an external cold water bath. Once hydrogen evolution had ceased, 1.00 mL (8.40 mmoles) of benzyl bromide was added dropwise to the reaction mixture, which was subsequently stirred at 10°–15° C. for 15 minutes and then at room temperature for 2 hours. After cautious addition of a few drops of water to destroy any excess sodium hydride, the mixture was diluted with 35 mL of hexane and washed in successive order with 10% aqueous sodium chloride (40 mL), 3:1 (v/v) $H_2O$: methyl alcohol (40 mL) to remove unreacted alkynol, and then with saturated brine (40 mL). The organic layer was then dried over anhydrous magnesium sulfate and subsequently filtered. Removal of the volatile organic solvents by evaporation at reduced pressure afforded 1.44 g (99% yield) of the named benzyl ether, whose structural integrity was verified by IR and proton NMR analysis.

EXAMPLE XIV

Preparation of 2-Benzyloxy-6,10,14-trimethyl-4-pentadecyn-6-ol

To a solution of 920 mg (5.28 mmoles) of 4-benzyloxy-1-pentyne (produced in accordance with Example XIII) and 0.25 mL (200 mg, 1.01 mmoles) of 6,10-dimethyl-2-undecanone (produced in accordance with Example XII) in 3.00 mL of dimethyl sulfoxide (HPLC-grade) was added 55 mg (0.49 mmole) of potassium tert-butoxide. This mixture was subsequently stirred, while being continuously maintained under a nitrogen atmosphere, at room temperature for 1.5 hours. At that point, a second 0.25 mL portion (200 mg, 1.01 mmoles) of 6,10-dimethyl-2-undecanone was added to the reaction mixture and stirring was continued at room temperature for an additional 3 hours. Isolation of the product as described in the procedure of Example I, followed by fractional distillation [25°–95° C. (bath temperature, 0.25 mm)] to remove unreacted starting materials, afforded 130 mg (17% yield) of the named alkynol, the identity of which was ascertained by IR and proton NMR analysis.

EXAMPLE XV

Preparation of 6,10-Dimethyl-9-undecen-4-yn-2,6-diol

A solution of 0.50 mL (5.3 mmoles) of 4-pentyn-2-ol (purchased from Aldrich Chemical Co., Milwaukee, Wis.) in 3.00 mL of dimethyl sulfoxide (HPLC-grade) was added dropwise slowly over 10 minutes to 5.3 mmoles of sodium hydride (60% dispersion in mineral oil, which was removed prior to the reaction by washing with hexane), protected from atmospheric moisture and maintained at a temperature of 15° C. by use of an external cold water bath. [NOTE: On a larger scale, use of metallic sodium rather than sodium hydride would be preferred for conversion of 4-pentyn-2-ol to an alkoxide salt]. Once hydrogen evolution had ceased, 0.10 mL (0.68 mmole) of 6-methyl-5-hepten-2-one and 55 mg (0.49 mmole) of potassium tert-butoxide were added; and the mixture was stirred, while being continuously maintained under a nitrogen atmosphere, at room temperature for 80 minutes. At that point, a second portion (0.10 mL, 0.68 mmole) of 6-methyl-5-hepten-2-one was added and stirring was continued at room temperature for an additional 80 minutes prior to the addition of a third portion (0.10 mL, 0.68 mmole) of the C-8 ketone. The mixture was subsequently stirred at room temperature for an additional 2 hours. Isolation of the product as described in the procedure of Example I afforded, after evaporative distillation in the presence of 5 mg of $CaCO_3$ powder, 400 mg (93% yield) of the named alkynediol: boiling point 112°–128° C. (bath temperature, 0.30 mm). The identity and purity of this compound were ascertained by IR and proton NMR analysis.

On a larger scale, slow addition of the ketone to the reaction mixture over a prolonged time (several hours) would be preferred in lieu of its addition in portions.

Subsequent to the execution of this experiment, an identical one was conducted in the absence of any potassium tert-butoxide. Since the product was obtained in the same high yield, the alkynylation can be achieved without the presence of any base other than the sodium alkoxide derived from 4-pentyn-2-ol.

EXAMPLE XVI

Preparation of 6,10,14-Trimethyl-4-pentadecyne-2,6-diol

To a solution of 5.3 mmoles of the sodium alkoxide derived from 4-pentyn-2-ol (produced using sodium hydride and the alkynol in accordance with Example XV) in 3.00 mL of dimethyl sulfoxide (HPLC-grade) were added 0.25 mL (200 mg, 1.01 mmoles) of 6,10-dimethyl-2-undecanone (produced in accordance with Example XII) and 52 mg (0.46 mmole) of potassium tert-butoxide (probably unnecessary in view of the experimental results reported in Example XV). This mixture was stirred, while being continuously maintained under a nitrogen atmosphere, at room temperature for 100 minutes. At that point, a second portion (0.25 mL, 1.01 mmoles) of 6,10-dimethyl-2-undecanone was added and stirring was continued at room temperature for an additional 3.5 hours. Isolation of the product as described in the procedure of Example I afforded, after fractional evaporative distillation in the presence of 5 mg of $CaCO_3$ powder, 552 mg (97% yield) of the named alkynediol: boiling point 122°–147° C. (bath temperature, 0.25 mm). The identity and purity of this novel C-18 compound were ascertained by high-field (300 MHz) proton NMR analysis. The latter spectrum exhibited doublets at δ0.89 (9 H's, J=6.6 Hz, two methyls bonded to C-14 and one $CH_3$ bonded to C-10) and δ1.28 [3 H's, J=6.2 Hz, $CH_3CH(OH)$], a singlet at δ1.49 ($CH_3$ bonded to C-6) and a multiplet at δ3.97 (1 H, CHOH).

This novel C-18 alkynediol was a *very viscous* oil after distillation. Although no attempt was made to determine if it would crystallize, such an effort should be made to facilitate large-scale purification of the compound.

On a larger scale, slow addition of the C-13 ketone to the reaction mixture over a period of several hours would be preferred in lieu of its addition in portions.

Subsequent to the execution of this experiment, an identical one was conducted with the exception that the saturated C-13 ketone (6,10-dimethyl-2-undecanone) was replaced by two portions [each 0.25 mL (221 mg, 1.15 mmoles)] of the corresponding unsaturated C-13 ketone [6,10-dimethyl-3,5,9-undecatrien-2-one("pseudoionone"), produced as outlined by the reference in Example XII]. IR and proton NMR analysis of the product mixture (406 mg) obtained in the latter experiment confirmed the *consumption* of pseudoionone, but indicated that little (if any) of the desired unsaturated C-18 alkynediol had been produced.

EXAMPLE XVII

Preparation of 6,10,14-Trimethyl-6-pentadecen-4-yn-2-ol

The above-named enynol is a known precursor to isophytol, which is used to manufacture vitamin E. [Reference: S. Abe, Japanese Patent No. 26,656 (Dec. 23, 1963). See: *Chem. Abstracts,* 60, 6746e (1964)]. Although for large-scale preparation of isophytol, a selective dehydration of the 3° alcohol functionality in 6,10,14-trimethyl-4-pentadecyne-2,6-diol (produced in accordance with Example XVI) should be feasible to obtain directly this C-18 enynol, the following multistep process described below proved to be more suitable for small-scale experimentation.

A solution of 230 mg (0.814 mmole) of 6,10,14-trimethyl-4-pentadecyne-2,6-diol (produced in accordance with Example XVI) and 0.25 mL (2.65 mmoles) of acetic anhydride in 0.25 mL of pyridine (A.C.S. reagent-grade, purchased from Aldrich Chemical Co., Milwaukee, Wis.) was stirred, while being maintained under a nitrogen atmosphere, at room temperature for 8 hours. After destroying excess acetic anhydride by addition of 10 mL of ice-cold 1M aqueous sodium hydroxide, the mixture was diluted with 20 mL of hexane and 25 mL of 10% aqueous sodium chloride. The layers were then separated, and the organic layer washed in successive order with 1:1 (v/v) 1M aqueous sodium hydroxide: 10% aqueous sodium chloride (1×10 mL), 1:1 (v/v) 2M aqueous hydrochloric acid: saturated brine (2×20 mL), saturated aqueous sodium bicarbonate (1×10 mL), and saturated brine (1×10 mL). The washed organic layer was subsequently dried over anhydrous magnesium sulfate and filtered. Removal of the volatile organic material by evaporation at reduced pressure afforded 249 mg (94% yield) of 2-acetoxy-6,10,14-trimethyl-4-pentadecyn-6-ol (i.e., the product derived by selective acetylation of the 2° alcohol functionality in the starting alkynediol).

To a solution of 0.35 mL (2.51 mmoles) of triethylamine and 245 mg (0.755 mmole) of 2-acetoxy-6,10,14-trimethyl-4-pentadecyn-6-ol in 1.00 mL of dichloromethane, protected from atmospheric moisture and maintained at a temperature of approximately 5° C. by use of an external ice water bath, was added 0.10 mL (1.29 mmoles) of methanesulfonyl chloride. This mixture was subsequently stirred at 0° C. for 2 hours, after which several ice chips were added to quench the reaction. After dilution with 25 mL of 4:1 (v/v) hexane: ether, the organic layer was washed in successive order with 1:1 (volume/volume) 2M aqueous hydrochloric acid: saturated brine (2×20 mL), saturated aqueous sodium bicarbonate (1×20 mL), and saturated brine (1×25 mL). The washed organic layer was subsequently dried over anhydrous magnesium sulfate and filtered. Removal of the volatile organic material by evaporation at reduced pressure afforded 225 mg (97% yield) of a mixture of two enynes derived from elimination of the 3° alcohol functionality in the starting material. In order to characterize the two components in this product mixture, the acetate ester functionality (at C-2) was saponified by treatment with anhydrous potassium carbonate (171 mg, 1.24 mmoles) in a mixture of methyl alcohol (2.0 mL) and water (0.10 mL). After stirring the latter mixture at room temperature for 15 hours, it was diluted with 20 mL of 3:1 (v/v) hexane: ether and 25 mL of 10% aqueous sodium chloride. The layers were then separated, and the organic layer was washed with 20 mL of 10% aqueous sodium chloride. The washed organic layer was subsequently dried over anhydrous magnesium sulfate and filtered. Removal of the volatile organic material by evaporation at reduced pressure afforded 179 mg (93% yield) of a 2:1 mixture of 6,10,14-trimethyl-6-pentadecen-4-yn-2-ol and 6-[4,8-dimethyl-nonyl]-6-hepten-4-yn-2-ol respectively, both of which afford the same C-18 alcohol when subjected to catalytic hydrogenation: 6,10,14-trimethyl-2-pentadecanol, a known precursor to isophytol. The proton NMR spectrum of the major product exhibited a broad triplet (J=8Hz) at $\delta 5.6$ (vinyl H bonded to C-7), whereas the minor enynol was characterized by two broad peaks (2 vinyl hydrogens bonded to C-7) at $\delta 5.2$ and 5.15.

EXAMPLE XVIII

Base-Catalyzed Isomerization of 4-Pentyn-2-ol

A solution of 0.50 mL (5.3 mmoles) of 4-pentyn-2-ol (purchased from Aldrich Chemical Co., Milwaukee, Wis.) in 3.00 mL of dimethyl sulfoxide (HPLC-grade) was added dropwise slowly over 10 minutes to 5.3 mmoles of sodium hydride (60% dispersion in mineral oil, which was removed prior to the reaction by washing with hexane), protected from atmospheric moisture and maintained at a temperature of 15° C. by use of an external cold water bath. Once hydrogen evolution had ceased, 46 mg (0.41 mmole) of potassium tert-butoxide was added; and the mixture was subsequently stirred, while being continuously maintained under a nitrogen atmosphere, at room temperature for 2 hours. At that point, the mixture was diluted with 25 mL of pentane and 25 mL of saturated brine and the layers (after being mixed) were separated. The organic layer was then washed with saturated brine (1×25 mL), dried over anhydrous magnesium sulfate and filtered. Removal of the pentane by evaporation at reduced pressure afforded (due to the volatility and water-solubility of the C-5 unsaturated alcohols present in the product mixture) only 43 mg of material, shown by spectroscopic analysis to contain 3,4-pentadien-2-ol as a major component. The infrared spectrum of this mixture of alcohols exhibited a moderate absorption at 1960 cm$^{-1}$, a band which is characteristic of compounds possessing an allenic functionality. Such an absorption was also reported by J. Grimaldi, et al., Bull. Soc. Chim. Fr., 973-9 (1971) in the IR data published for 3,4-pentadien-2-ol. Since the spectral analysis indicated very little 4-pentyn-2-ol was present in the product mixture, the successful execution of the alkynylation process described in Example XVI is even more remarkable and perhaps indicates that the base-catalyzed isomerization of 4-pentyn-2-ol involves a reversible process.

What is claimed is:

1. A process for synthesizing a tertiary alkynol comprising:
    a) forming a reaction mixture in a non-hydroxylic organic solvent containing:
       i) a carbonyl-group-containing compound of the formula RCH$_2$COCH$_2$R$^1$;
       ii) an alkyne having the formula R$^{11}$C≡CH; and
       iii) a catalytic amount of a base stronger than an alkali-metal carbonate;
    wherein R and R$^1$ are alkyl or H or form part of an alicyclic ring; and R$^{11}$ is an alkyl, alkenyl, alkoxyalkyl, hydroxyalkyl or the alkali-metal salt thereof, aryl or arylalkyl group, provided that when either R or R$^1$ is H, said carbonyl-group-containing compound is slowly added to said reaction mixture, and when R or R$^{11}$ contains a carbon-carbon double bond, the double bond is not conjugated with the carbonyl group of said carbonyl-group containing compound; and
    b) maintaining said reaction mixture until said tertiary alkynol is formed.

2. The process of claim 1 wherein said alkyne is 4-pentyn-2-ol or a 2-oxy derivative thereof, and wherein said tertiary alkynol is 6,10,14-trimethyl-4-pentadecyne-2,6-diol or a 2-oxy derivative thereof and said base is an alkoxide.

3. The process of claim 1 wherein the carbonyl-group-containing-compound is cyclohexanone.

4. The process of claim 1 wherein the carbonyl-group-containing-compound is 6-methyl-5-hepten-2-one.

5. The process of claim 1 wherein R, R$^1$ or R$^{11}$ is a group having an ether functionality.

6. The process of claim 1 wherein R, R$^1$ or R$^{11}$ is a group having an acetal functionality.

7. The process of claim 1 wherein R$^{11}$ is a group having an unblocked 3° alcohol functionality.

8. The process of claim 1 wherein said alkyne comprises 2-methyl-3-butyn-2-ol.

9. The process of claim 1 wherein R$^{11}$ is a group having an alkoxide functionality.

10. The process of claim 1 wherein said alkyne comprises

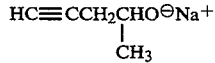

11. The process of claim 1 wherein the alkyne has the structure:

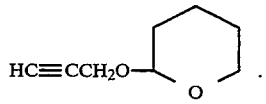

12. The process of claim 1 wherein said carbonyl-group-containing compound is a C-13 ketone and said alkyne is 4-pentyn-2-ol.

13. The process of claim 1 wherein said carbonyl-group-containing compound is a C-13 ketone and said alkyne is the sodium salt of 4-pentyn-2-ol.

14. The process of claim 1 wherein said carbonyl-group-containing compound is cyclohexanone and said alkyne is 1-octyne.

15. The process of claim 1 wherein said carbonyl-group-containing compound is cyclohexanone and said alkyne is 1-hexyne.

16. The process of claim 1 wherein said carbonyl-group-containing compound is 3-pentanone and said alkyne is phenylacetylene.

17. The process of claim 1 wherein said carbonyl-group-containing compound is cyclohexanone and said alkyne is 2-methyl-3-butyn-2-ol.

18. The process of claim 1 wherein said carbonyl-group-containing compound is cyclohexanone and said alkyne is 3-[(tetrahydropyran-2-yl)oxy]propyne.

19. The process of claim 1 wherein said alkyne comprises an ether formed by reacting 4-pentyn-2-ol with a blocking agent.

20. The process of claim 19 wherein said blocking agent is benzyl chloride.

21. The process of claim 1 wherein said base is an alkali-metal alkoxide.

22. The process of claim 21 wherein said base is selected from the group consisting of potassium tertbutoxide, sodium tert-butoxide, potassium methoxide and mixtures thereof.

23. The process of claim 1 wherein said base comprises sodium tert-butoxide and a soluble potassium salt.

24. The process of claim 23 wherein said potassium salt is potassium acetate or potassium chloride.

25. The process of claim 1 wherein said base comprises powdered KOH.

26. The process of claim 1 wherein said base comprises an alkali-metal salt of said alkyne reactant.

27. The process of claim 1 wherein said base comprise an alkoxide of the formula:

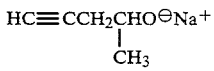
|
$CH_3$

28. The process of claim 1 wherein the reactant having the structure

is a C-13 carbonyl-group-containing compound.

29. The process of claim 1 wherein said organic solvent comprises a polar, aprotic liquid.

30. The process of claim 29 wherein the polar, aprotic solvent is selected from the group consisting of dimethyl sulfoxide, 1-methyl-2-pyrrolidinone and acetonitrile.

31. The process of claim 1 wherein said organic solvent comprises a non-polar organic liquid, further including the step:
heating said reaction mixture to a temperature of less than 100° C.

32. The process of claim 31 wherein said solvent is selected from the group consisting of tetrahydrofuran and benzene.

33. The process of claim 1, wherein said solvent comprises a polar, aprotic liquid, further including the step:
heating said reaction mixture to a temperature from about 50° C. to about 60° C.

* * * * *